United States Patent
Reddy et al.

[11] Patent Number: 5,808,039
[45] Date of Patent: Sep. 15, 1998

[54] 2'-OME C^AC PHOSPHORAMIDITE AND METHODS FOR PREPARATION AND USE THEREOF

[75] Inventors: Meda Parameswara Reddy; Firdous Farooqui, both of Brea; Naeem B. Hanna, Fullerton, all of Calif.

[73] Assignee: Beckman Instruments, Inc., Fullerton, Calif.

[21] Appl. No.: 546,165

[22] Filed: Oct. 18, 1995

[51] Int. Cl.⁶ .............................. C07H 21/00; C07H 19/06
[52] U.S. Cl. .................. 536/25.3; 536/25.31; 536/25.34; 536/25.4; 536/26.8
[58] Field of Search ................. 536/26.8, 25.34, 536/25.3, 25.31, 25.4

[56] References Cited

U.S. PATENT DOCUMENTS

| | | | |
|---|---|---|---|
| 5,214,135 | 5/1993 | Srivastava et al. | 536/26.7 |
| 5,348,868 | 9/1994 | Reddy et al. | |
| 5,428,148 | 6/1995 | Reddy et al. | |
| 5,525,719 | 6/1996 | Srivastava et al. | 536/26.7 |

OTHER PUBLICATIONS

Agrawal, Sudhir et al. *Oligodeoxynucleoside Methylphosphonates: Synthesis and Enzymic Degradation* (1987) Tetrahedron Letters, vol. 28, No. 31 pp. 3539–3542.
Beijer, B. et al., *Nucleic Acids Research* (1990) 18, 5143–5151.
Bhat, U. et al., *Nucleoside and Necleotides* (1989) 8, 179–183.
Chanteloup, L. and Thuong, N., *Tetrahedron Letters* (1994) 35, 877–880.
Chattopadhyaya, J. et al., *Acta Chem. Scand.* (1986) B40, 826–830.
Cotten, M. et al., *Nucleic Acids Research* (1991) 19, 2629–2635.
Inoue, H. et al., *Nucleic Acids Research* (1987) 15, 6131–6148.
Inoue H. et al., *Nucleic Acids Research* Symposium Series (1985) 16, 165–168.
Lamond, I.A. et al. *FEWBS Letters* (1993) 325, 123–127.
Reddy, M.P. et al., *Tetrahedron Lett.* (1994) 25, 4311–4314.
Ross, B.S. et al., *J. Heterocyclic Chem.* (1994) 31, 765–769.
Shimizu, M. et al., *FEBS Letters* (1992) 302, 155–158.
Sinha, N.D. et al., *Nucleic Acids Research* (1984) 12, 4538–4557.
Sproat, B.S. et al., *Nucleic Acids Research* (1990) 18, 41–49.
Vaghefi, M. et al. *Nucleosides and Nucleotides* (1993) 12, 1007–1013.

*Primary Examiner*—James O. Wilson
*Attorney, Agent, or Firm*—William H. May; P. R. Harder; Margaret A. Kivinski

[57] ABSTRACT

A compound of the general formula

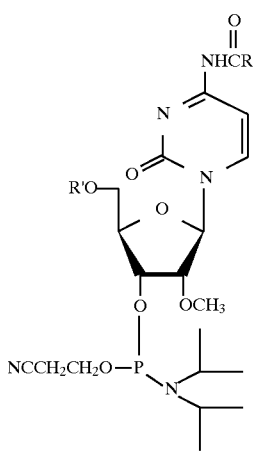

wherein R is alkyl of 1 to about 10 carbons and R' is selected from the group consisting of trityl and pixyl, for use in the synthesis of 2'-OMe RNA sequences. Fast cleavage and deprotection of oligonucleotides is facilitated by the use of a reagent comprising methylamine as active component in place of the traditional reagent ammonium hydroxide.

4 Claims, No Drawings

2'-OME $C^{Ac}$ PHOSPHORAMIDITE AND METHODS FOR PREPARATION AND USE THEREOF

BACKGROUND OF THE INVENTION

The present invention relates generally to the fields of chemistry and biology. In particular, the present invention is directed to compositions and methods for use in synthesis of oligonucleotides.

Oligonucleotides containing 2'-OMe ribonucleotides of the formula

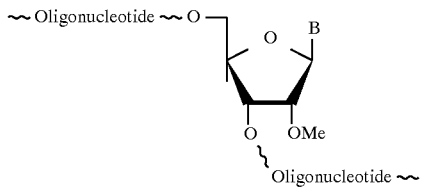

have widespread applications in both diagnostics and therapeutics, in particular because of their strong affinity for complementary strands and resistance toward unwanted nuclease degradation. Further, they possess high chemical stability and are resistant to hydrolysis by alkali and nucleases [Inoue H. et al., *Nucleic Acids Research* Symposium Series (1985) 16, 165–168; Cotten M. et al., *Nucleic Acids Research* (1991) 19, 2629–2635]. Oligo-2'-O-alkyl ribonucleotides hybridize specifically and strongly to RNA sequences and to duplex DNA via triplex formation [Lamond, I. A and Sproat B. S. *FEBS Letters* (1993) 325, 123–127; Shimizu, M et al, *FEBS Letters* (1992) 302, 155–158]. Of particular interest to researchers is the use of 2'-OMe RNA in antisense probes for studying site specific inhibition of mRNA splicing. The preparation of mixed oligoribonucleotides containing 2'-OMe ribonucleotides at specific points has been described, along with their significance in the study of RNA-protein interactions and their application to the synthesis of ribozymes [Beijer, B. et al., *Nucleic Acids Research* (1990) 18, 5143–5151].

5'-DMT-2'-OMe ribonucleoside-3'-cyanoethyl phosphoramidite monomers have typically been employed for the synthesis of 2'-OMe RNA sequences. Several alternative methods have been developed to synthesize the monomers [Chanteloup, L. and Thuong, N., *Tetrahedron Letters* (1994) 35, 877–880; Sproat, B. S. et al., *Nucleic Acids Research* (1990) 18, 41–49; Ross, B. S. et al., *J. Heterocyclic Chem.* (1994) 31, 765–769; Vaghefi, M. and Hogrefe, R., *Nucleosides and Nucleotides* (1993) 12, 1007–1013; Inoue H. et al, *Nucleic Acids Research* (1987) 15, 6131–6148].

Synthesis of 2'-OMe RNA is usually performed on a solid support. Internucleotide coupling requires a fairly long time of about 15 minutes, mainly due to steric hindrance from the 2'-OMe group. The 2'-OMe group remains stable toward the basic cleavage and deprotection conditions. As 2'-OMe containing RNA sequences are resistant to nuclease hydrolysis, purification is typically performed by standard techniques used in conventional DNA synthesis; special precautions, such as the use of sterile conditions as for the processing of RNA, are not necessary. Nonetheless, there remains a need for improved methods which are more rapid and/or produce fewer side-products.

It is an object of the present invention to provide methods for synthesis of 2'-OMe RNA sequences which do not suffer from all of the drawbacks of prior art methods.

SUMMARY OF THE INVENTION

In accordance with the present invention, there are provided compounds of the general formula I

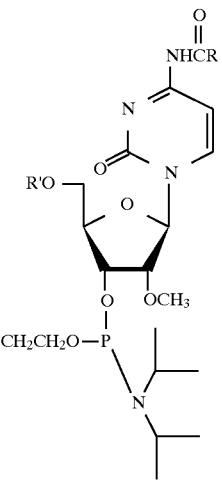

wherein R is methyl and R' is selected from the group consisting of trityl and pixyl, for use in the synthesis of 2'-OMe RNA sequences. Fast cleavage and deprotection of oligonucleotides is facilitated by the use of methylamine or a mixture of methylamine/ammonium hydroxide in place of the traditional reagent ammonium hydroxide.

DETAILED DESCRIPTION OF THE INVENTION

Pursuant to the present invention, a composition comprising methylamine as active component (e.g., methylamine or a mixture of methylamine/ammonium hydroxide) is employed for deprotection in place of the traditional reagent ammonium hydroxide [Reddy, M. P. et al., *Tetrahedron Lett.* (1994) 25, 4311–4314; U.S. Pat. Nos. 5,348,868; 5,428,148]. While ammonium hydroxide takes 60 minutes at room temperature to cleave the oligonucleotides from the solid support (through the hydrolysis of the ester linkage through which the oligonucleotide is attached to the solid support) on which the oligonucleotide is synthesized, use of methylamine or methylamine/ammonium hydroxide in accordance with the present invention reduces the cleavage time to about 5 minutes at room temperature. Similarly, the removal of the protecting groups on the heterocyclic nucleoside base, which takes about 3 hours at 65° C. with ammonium hydroxide, has been reduced to a 5 minute process by the use of methylamine or methylamine/ammonium hydroxide. Compositions comprising methylamine and methylamine/ 29% ammonium hydroxide mixtures suitable for use in deprotection are described in detail in the aforementioned U.S. Pat. Nos. 5,348,868 and 5,428,148, the entire disclosures of which are hereby incorporated by reference. Typically, methylamine is employed in the commercially-available 40% solution. Ammonium hydroxide is typically used in a 1:1 volume ratio with the methylamine solution; a concentrated solution of 29% ammonia as is commercially available may suitably be employed for this purpose. Other suitable components for admixture with methylamine include, but are not limited to, alcohols (e.g., ethanol, methanol, etc.), acetonitrile, water, etc.

In order to avoid transamination side product formation as observed with the conventional $dC^{bz}$ or $dC^{ibu}$ derivatives when using a methylamine cleavage system, $dC^{Ac}$ phosphoramidites are conveniently employed. Use of a compound of general formula I such as 5'-DMT $dC^{Ac}$ 3'-cyanoethylphosphoramidite for DNA synthesis in the place of 5'-DMT $dC^{bz}$ 3'-cyanoethylphosphoramidite completely eliminates unwanted transamination side products, while making it possible effectively to take advantage of the fast kinetics achieved with the methylamine system.

In accordance with the present invention, DMT $C^{Ac}$-2'-OMe-3'-cyanoethylphosphoramidite ("$C^{Ac}$ 2'-OMe phosphoramidite") of the formula

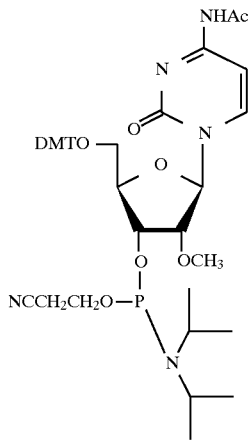

was synthesized as depicted in Scheme I. Cytidine (1) was quantitatively converted to 2 by a selective acetylation procedure [Bhat, U. et al., *Nucleoside aid Nucleotides* (1989) 8, 179–183)]. $N^4$-Acetylcytidine 2 was reacted with 1,3-dichloro- 1,1,3,3-tetraisopropyldisiloxane to give $N^4$-acetyl-3,5'-O-tetraisopropyldisiloxane-1,3-diyl-cytidine (3) in 90% yield. Treatment of 3 with excess MeI/Ag$_2$O [Inoue, H. et al., *Nucleic Acids Research* (1987) 15, 6131–6148] in dry benzene at room temperature afforded 60% of the 2'-O-methyl derivative (4) after column chromatography. Removal of the silyl groups using Bu$_4$NF in THF at room temperature gave $N^4$-acetyl-2'-O-methyl cytidine (5) in 42% yield after work up according to literature procedure [Chattopadhyaya, J. et al., *Acta Chem. Scand.* (1986) B40, 826–830]. The compound 5 was tritylated with 1.2 equivalents of 4,4'-dimethoxytrityl chloride in pyridine at 5° C. for 20 hours to yield the DMT-2'-O-methylcytidine derivative 6 in 65% yield. Phosphorylation of 6 with 2 equivalents of β-cyanoethyl N,N-diisopropylmonochlorophosphoramidite [Sinha, N. D. et al., *Nucleic Acids Research* (1984) 12, 4539–4537] in tetrahydrofuran in the presence of 4 equivalents of N,N,N-diisopropylethylamine afforded 60% yield of 5'-DMT-$N^4$-acetyl-2'-O-methylcytidine-3'-phosphoramidite 7.

SCHEME I

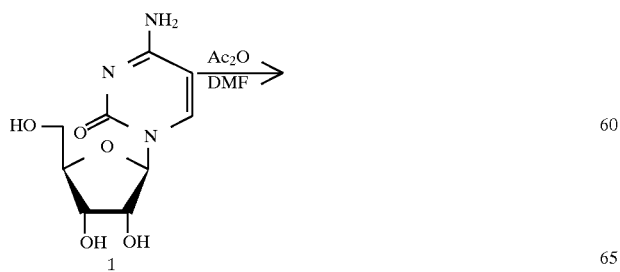

-continued
SCHEME I

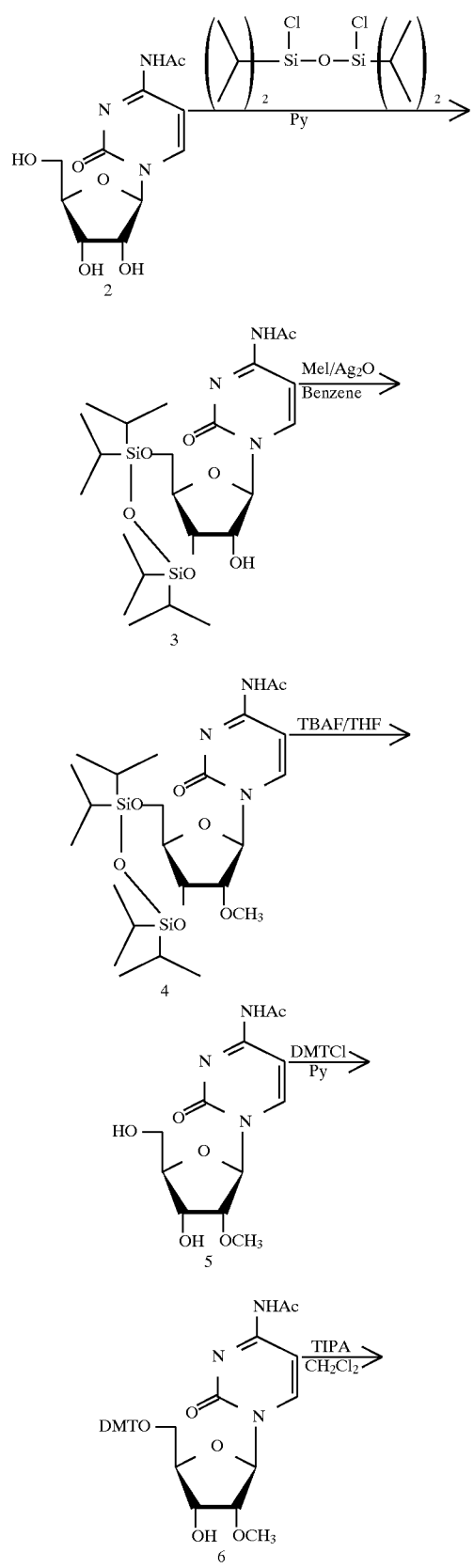

-continued
SCHEME I

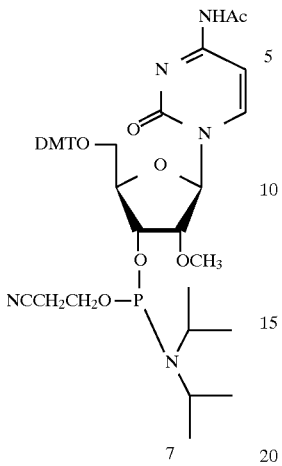

$C^{Ac}$ 2'-OMe phosphoramidite 7 was successfully utilized in the synthesis of 2'-OMe oligonucleotides on an automated DNA synthesizer using a 15 minute coupling time. After the solid phase synthesis of 21 mer and 35 mer sequences, they were cleaved with methylamine (40% aqueous solution, as commercially available from Aldrich Chemical Company) for 5 minutes at room temperature and deprotected by incubation with the same reagent at 65° C. for 5 minutes. Alternatively, deprotection was also performed at room temperature for 90 minutes. The 2'-OMe oligoribonucleotides were analyzed by capillary gel electrophoresis, HPLC and Tm analysis. They were practically indistinguishable from the same oligoribonucleotide sequences synthesized by conventional methods. No transamination side products were observed with the use of $C^{Ac}$ phosphoramidite. As heretofore described, use of the cytidine $C^{bz}$ or $C^{ibu}$ derivative produces 10% and 0.7% of transamination side products, respectively. These side products can be detrimental, especially for therapeutic applications.

The invention may be better understood with reference to the accompanying examples, which are intended for purposes of illustration only and should not be construed as in any sense limiting the scope of the invention as defined in the claims appended hereto.

EXAMPLE 1

$N^4$-Acetylcytidine (2)

Cytidine (1) (7.3 g, 30 mmoles) was suspended in anhydrous N,N-dimethylformamide (120 ml) and to it was added acetic anhydride (3.12 ml, 33 mmoles). The mixture was stirred at room temperature overnight. After removal of the DMF under reduced pressure, the resulting residue was triturated with excess of diethylether (~30 ml) and the crystalline product obtained collected by filtration, washed thoroughly with diethylether and air dried to get a quantitative yield of 2. A small portion was crystallized from ethanol/water mixture (1:1) to obtain crystals for analytical purposes.

m.p. 210°–213° C. (dec.).

UV ($H_2O$): λ max 296 nm and 246 nm.

IR (KBr): ν1637 (vs, CO of ring amide), 1721 (s, CO of acetamide), and 2900–3600 (NH, OH) $cm^{-1}$.

$^1$H-NMR (DMSO-$d_6$): δ2.10 (s, 3H, $COCH_3$), 3.65 (m, 2H, $C_5·CH_2$), 3.91–3.97 (m, 3H,$C_{2',3',4'}$H), 5.06–5.51 (m, 3H, $C_{2',3',5'}$—OH), 5.78 (s, 1H, $C_1$H), 7.18 (d, 1H, $C_5$H), 8.42 (d, 1H, $C_6$H), and 10.90 (s, 1H, CONH).

EXAMPLE 2

3',5'-O-(Tetraisopropyldisiloxane-1,3-diyl-$N^4$-acetylcytidine (3)

To a solution of $N^4$-acetylcytidine (2) (10 g, 35.6 mmoles) in dry pyridine (100 ml) 1,1,3,3-tetraisopropyl-1,3-dichlorosiloxane (12 g, 38.5 mmoles) was added. After 15 hours at room temperature, water (200 ml) was added and the reaction mixture was extracted with methylene chloride (2×300 ml). The organic layer was dried over anhydrous $Na_2SO_4$ and evaporated to dryness. The residue was purified by flash silica gel chromatography in a 5×40 cm column packed in $CH_2Cl_2$. The column was eluted with 800 ml portions of gradient 2–8% MeOH/$CH_2Cl_2$. The desired fractions were pooled, evaporated, and dried over $P_2O_5$ to give 16.65 g (90% yield) of 3 as a foam.

UV (EtOH): λ max 298 nm and 248 nm.

$^1$H-NMR (CDCl$_3$): δ 0.97–1.10 (m, 28H, $CH_3$ of iPr), 2.30 (s, 3H, $COCH_3$), 3.30 (br, s, 1H, $C_{2'}$,OH), 4.19–4.30 (m, 5H,$C_{1',3',4',5'}$H), 5.82 (s, 1H, $C_1$,H), 7.44 (d, 1H, $C_5$H), 8.20 (d, 1H, $C_6$H), and 9.97 (br, s, 1H, NHCO).

HPLC: 98.5% purity.

EXAMPLE 3

3',5'-O-(Tetraisopropyldisiloxane-1,3-diyl)-2'-O-methyl-$N^4$-acetylcytidine (4)

A mixture of 3 (5.63 g, 10.67 mmoles), $CH_3I$ (15 ml, 242 mmoles) and $Ag_2O$ (8.4 g, 39 mmoles) in dry benzene (60 ml) was stirred at room temperature, overnight. The reaction mixture was filtered through a short layer (1 cm) of celite and washed with $CH_2Cl_2$; the filtrate was concentrated in vacuo. The residue was chromatographed on a silica gel column (2.5×50 cm) packed in $CH_2Cl_2$ and eluted with 200 ml portions of gradient 0–5% MeOH/$CH_2Cl_2$. The desired fractions were pooled, evaporated and dried over $P_2O_5$ to give 3.47 g (60% yield) of 4 as a solid.

UV (EtOH): λ max 298 nm and 248 nm.

$^1$H-NMR (CDCl$_3$): δ 0.96–1.11 (m, 28H, $CH_3$ of iPr), 2.51 (s, 3H, $COCH_3$), 3.65 (s, 3H, 2'-$OCH_3$), 3.95–4.45 (m, 5H,$C_{1',3',4',5'}$H), 5.77 (s, 1H, $C_1$,H), 7.22 (d, 1H, $C_5$H), and 7.93 (d, 1H, $C_6$H).

EXAMPLE 4

$N^4$-Acetyl-2'-O-methylcytidine (5)

Compound 4 (1.3 g, 2.4 mmoles) was dissolved in dry tetrahydrofuran (10 ml) and tetrabutylammonium fluoride in tetrahydrofuran (1M, 6 ml) added at room temperature. After 20 minutes, the reaction mixture was concentrated. The residue was dissolved in distilled water (20 ml) and extracted with dichloromethane (2×30 ml). The aqueous layer was washed with diethylether (2×30 ml) and concentrated. The oily residue was purified on a flash silica gel column (2×20 cm) packed in $CH_2Cl_2$ and eluted with 200 ml portions of gradient 2–8% MeOH/$CH_2Cl_2$. The desired fractions were pooled and evaporated. The product was crystallized from MeOH/$CH_2Cl_2$ to give (5) (0.30 g, (42% yield).

m.p. 220°–223° C. (dec.)

UV ($H_2O$): λ max 298 nm and 248 nm.

$^1$H-NMR (DMSO-$d_6$): δ 2.10 (s, 3H, $COCH_3$), 3.46 (s, 3H, 2'-$OCH_3$), 3.71–4.05 (m, 5H, $C_{2',3',4',5'}$H), 5.11 (d, 1H, $C_{5'}OH$, exchangeable with $D_2O$), 5.22 (t, 1H, $C_{3'}OH$, exchangeable with $D_2O$), 5.84 (s, 1H, $C_1,H$), 7.19 (d, 1H, $C_5H$) 8.47 (d, 1H, $C_6H$), and 10.97 (br, s, 1H, NHCO, exchangeable with $D_2O$).

HPLC: 98% purity.

EXAMPLE 5

5'-O-(4,4'-Dimethoxytrintyl)-N⁴-acetyl-2'-O-methylcytidine (6)

Compound 5 (0.6 g, 2 mmoles) was dried by coevaporation with dry pyridine and dissolved in 15 ml of pyridine. To the stirred solution of 5 at 0° C., 4,4'-dimethoxytrityl chloride (0.81 g, 2.4 mmoles) was added and stirred for 15 hours at 0° C. The solution was evaporated, the residue was dissolved in $CH_2Cl_2$ (50 ml) and extracted with 6% $NaHCO_3$ solution (2×30 ml) and the organic layer was dried over anhydrous $Na_2SO_4$ and filtered. The product was purified on a flash silica gel column (2.5×30 cm) packed in $CH_2Cl_2$ and eluted with 200 ml portions of gradient 2–8% $MeOH/CH_2Cl_2$. The desired fractions were pooled, evaporated and dried to give 6, 0.78 g (65% yield).

UV(EtOH): λ max 300 nm 282 nm and 234 nm.

$^1$H-NMR ($CDCl_3$): δ 2.22 (s, 3H, $COCH_3$), 3.60 (m, 2H, $C_5,CH_2$), 3.77 (s, 3H, 2'-$OCH_3$), 3.82 (s, 6H, 2×$OCH_3$), 3.74 (m,1H, $C_4$H), 4.02 (m, 1H, $C_3$H), 4.41 (m,1H, $C_2,H$), 6.00 (s, 1H, $C_1,H$), 6.85–7.40 (m, 13H, DMT group), 7.06 (d, 1H, $C_5H$), 8.53 (d, 1H, $C_6H$), and 8.98 (br, s, 1H, NHCO).

HPLC: 98% purity.

EXAMPLE 6

5'-O-(4,4'-Dimethoxytrityl)-N⁴-acetyl-2'-O-methylcytidine-3'-O-(N,N-diisopropyl)-β-cyanoethyl-phosphoramidite (7)

Compound 6 (1.2 g, 2 mmoles) was dried by successive coevaporations with dry pyridine, toluene and THF. The dried residue was dissolved in dry THF (10 ml) and redistilled N,N,N-diisopropylethylamine (1.7 ml, 8 mmoles) was added, followed by the addition of N,N-diisopropyl-monochloro-β-cyanoethylphosphoramidite (1.2 ml) dropwise under argon for 5 minutes. After 15 hour of stirring, the reaction mixture was diluted with ethyl acetate (50 ml), washed with 6% $NaHCO_3$ solution (2×40 ml) and dried over $Na_2SO_4$. The crude material was dissolved in ethyl acetate and transferred to a silica gel column (2.5×30 cm, 70–230 mesh, 60 A, preheated at 100°–120° C., overnight) and eluted with ethyl acetate. The desired fractions were pooled and evaporated to dryness under high vacuum to yield phosphoramidite (7) in 50% yield (0.8 g).

UV(EtOH): λ max 300 nm 284 nm and 236 nm.

IR (KBr): v1660 (vs, CO of ring amide), 1720 (s, CO of acetamide),2256 (CN groups), and 3000 (br, s, NH) cm$^{-1}$.

$^1$H-NMR ($CDCl_3$): δ 0.86–1.26 (m, 12H, $CH_3$iPr), 2.22 (s, 3H, $COCH_3$),2.41 and 2.62 (2t, 4H,—$CH_2CH_2CN$) 3.45–4.29 (m, 16H, $C_5,CH_2$, 2×CH iPr, 2'-$OCH_3$, 2×$OCH_3$, $C_{2',3',4'}$H) 6.02 (2s,1H, $C_1,H$), 6.83–7.43 (m, 14H, DMT aromatic protons and $C_5H$), 8.62 (d, 1H, $C_6H$), and 9.31 (br, s, 1H, NHCO).

$^{31}$P-NMR ($CDCl_3$): δ148.783 ppm and 149.428 ppm.

HPLC: Retention times of 7.81 and 8.73 corresponding to the two diastereisomers (98% purity). Conditions: $C_{18}$ Microsorb (Rainin column) $S_4$ particles 4.6 mm×25 cm. Bottle A: 0.1M ammonium acetate (pH 6.9 ), Bottle B: Acetonitrile. Program Flow rate 1 ml/min 0–20 min at 80% B.

EXAMPLE 7

Synthesis of Oligonucleotides using 2'-OMe $C^{Ac}$ phosphoramidite 21 mer sequence: $^{5'}$CTGGACAGTAGTCAGACTGCT$^{3'}$ 35 mer sequence: $^{5'}$GATGCCAGTTCGGTCATACACG-TAGTACTACGACT$^{3'}$ Oligomers (21 mer and 35 mer sequences) were synthesized on a Beckman Oligo 1000 instrument on T-CPG support using 2'-OMe $C^{Ac}$ phosphoramidite and conventional materials as the other three 2'-OMe phosphoramidites. The coupling time was 15 minutes. After synthesis, the oligonucleotide was cleaved with methylamine for 5 minutes at room temperature and deprotected for 5 minutes at 65° C. The product was analyzed by reverse phase HPLC and Capillary electrophoresis. Comparison with materials prepared using conventional starting materials confirmed that the products were virtually indistinguishable.

From the foregoing description, one skilled in the art can readily ascertain the essential characteristics of the invention and, without departing from the spirit and scope thereof, can adapt the invention to various usages and conditions. Changes in form and substitution of equivalents are contemplated as circumstances may suggest or render expedient, and although specific terms have been employed herein, they are intended in a descriptive sense and not for purposes of limitation.

What is claimed is:

1. A compound of general formula

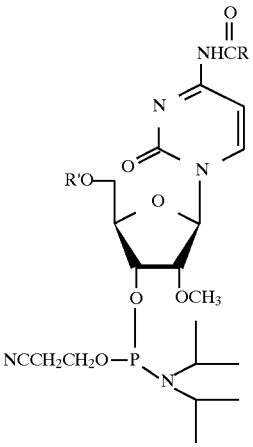

wherein R is methyl and R' is selected from the group consisting of a trityl or pixyl moiety.

2. A compound according to claim 1, which is DMT $C^{Ac}$-2'-OMe-3'-cyanoethylphosphoramidite.

3. In a method of synthesizing an oligonucleotide sequence containing 2'-OMe ribonucleotides by addition of nucleosides to a solid phase support followed by deprotection and cleavage of a completed sequence from the support, the improvement comprising use of a compound of general formula

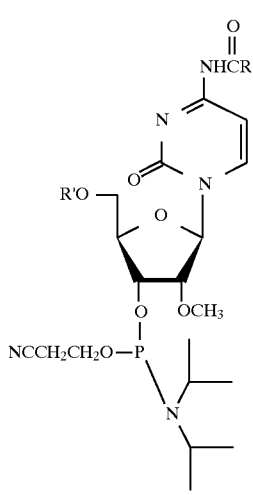
wherein R is methyl and R' is selected from the group consisting of a trityl or pixyl moiety.
4. A method according to claim 2, wherein deprotection is effected using a reagent comprising methylamine as active component.
* * * * *